United States Patent [19]

Tjoeng et al.

[11] Patent Number: 5,710,166

[45] Date of Patent: Jan. 20, 1998

[54] N-ACYL BETA AMINO ACID DERIVATIVES USEFUL AS PLATELET AGGREGATION INHIBITORS

[75] Inventors: Foe S. Tjoeng, Manchester; Mihaly V. Toth, St. Louis, both of Mo.

[73] Assignee: The Monsanto Company, St. Louis, Mo.

[21] Appl. No.: 518,660

[22] Filed: Aug. 24, 1995

Related U.S. Application Data

[63] Continuation of Ser. No. 24,977, Mar. 2, 1993, abandoned.

[51] Int. Cl.$^6$ .................... A61K 31/445; C07D 401/12; C07D 211/56
[52] U.S. Cl. ................. 514/318; 514/357; 514/637; 546/194; 546/332; 564/246
[58] Field of Search .................... 546/194, 332; 564/246; 514/318, 357, 637

[56] References Cited

U.S. PATENT DOCUMENTS

| | | | |
|---|---|---|---|
| 4,962,101 | 10/1990 | DiNinno et al. | 514/210 |
| 5,039,805 | 8/1991 | Alig et al. | 546/224 |
| 5,220,050 | 6/1993 | Bovy | 514/357 |
| 5,239,113 | 8/1993 | Bovy | 562/440 |
| 5,254,573 | 10/1993 | Bovy | 514/357 |
| 5,344,957 | 9/1994 | Bovy | 560/35 |

OTHER PUBLICATIONS

Banner et al. "Serine proteases:3D structures, mechanisms of action and inhibitors" Perspect. Med. Chem. Verlag, pp.27–43, 1993.

Hartman et al "Nonpeptide Fibrinogen Receptor Antagonist" J. Med. Chem. 35 4640–4642 (1992).

Rubini et al "Synthesis of Isosteric Methylene–oxy Pseudopeptide Analogues as Novel Amide Surrogate Units" Tetrahedron 42 6039–45 (1986).

*Primary Examiner*—Ceila Chang
*Attorney, Agent, or Firm*—Cynthia S. Kovacevic; Roger A. Williams

[57] ABSTRACT

Novel N-Acyl Beta Amino Acid derivatives of the formula

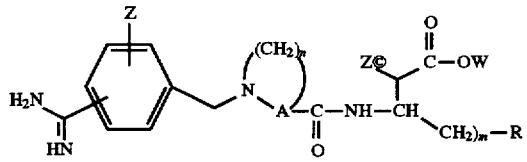

are provided which inhibit platelet aggregation. This invention also pertains to pharmaceutical compositions and methods of using such derivatives.

6 Claims, No Drawings

N-ACYL BETA AMINO ACID DERIVATIVES USEFUL AS PLATELET AGGREGATION INHIBITORS

This is a File-Wrapper Continuation of application Ser. No. 08/024,977, filed Mar. 2, 1993 now abandoned.

BACKGROUND OF THE INVENTION

1. Field of the Invention

This invention pertains to N-acyl beta amino acid derivatives which inhibit platelet aggregation in mammals.

2. Related Art

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb/IIIa; this is an important feature of the platelet function. Inhibitors of this interaction are useful in modulating or preventing platelet thrombus formation.

It is also known that another large glycoprotein named fibronectin, which is a major extracellular matrix protein, interacts with fibrinogen and fibrin, and with other structural molecules such as actin, collagen and proteoglycans. Various relatively large polypeptide fragments in the cell-binding domain of fibronectin have been found to have cell-attachment activity. (See U.S. Pat. Nos. 4,517,686, 4,589,881, and 4,661,111). Certain relatively short peptide fragments from the same molecule were found to promote cell attachment to a substrate when immobilized on the substrate or to inhibit attachment when in a solubilized or suspended form. (See U.S. Pat. Nos. 4,578,079 and 4,614,517).

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Koczewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Pierschbacher, *Science* 238, 491–497 (1987). Still other such inhibitory peptides are disclosed in EP Patent Applications 275,748 and 298,820.

U.S. Pat. No. 4,879,313 discloses guanidino substituted alkanoic acid derivatives which inhibit protein to receptor binding and are useful for the treatment of thrombosis and cardiac infarction.

European Patent Application 372,486 discloses N-acyl beta amino acid derivatives and their salts. Said compound are useful for inhibiting platelet aggregation in the treatment of thrombosis, stroke, myocardial infarction, inflammation and arterioschlerosis, and for inhibiting metastasis.

European Patent Application 381,033 discloses alkanoic acid derivatives useful for the treatment of thrombosis, apoplexy, cardiac infarction, inflammation, arteriosclerosis and tumors.

European Patent Application 445,796 discloses Acetic Acid derivatives useful as a ligand for adhesive proteins on platelets. As such these compounds are useful to modulate and/or inhibit platelet aggregation.

European Patent Application 513,810 discloses amidinoaryl substituted alkanoic acid derivatives which have usefulness as inhibitors of platelet aggregation.

The disclosure of all references cited in this application is hereby incorporated by reference.

SUMMARY OF THE INVENTION

The present invention relates to a class of compounds represented by the formula:

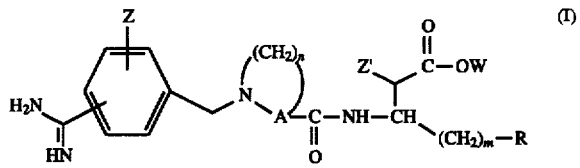

or a pharmaceutically acceptable salt thereof, wherein R is independently selected from the group consisting of hydrogen, lower alkyl radicals, lower alkenyl radicals, lower alkynyl radicals, alicyclic hydrocarbon radicals, and aromatic hydrocarbon radicals, wherein all of said radicals are optionally substituted with hydroxyl, lower alkoxy, lower alkyl, halogen, nitro, carboxyl, trifluoromethyl, amino, acyloxy, phenyl and naphthyl which are optionally substituted with halogen, nitro, lower alkoxy, and lower alkyl;

or R is a monocyclic or bicyclic heterocyclyl radical in which 1 to about 3 heteroatoms are independently selected from nitrogen, oxygen or sulfur and said heterocyclyl radicals may be optionally substituted with one or more groups selected from alkyl having 1 to 6 carbon atoms, alkoxy having 1 to 6 carbon atoms, halo, and hydroxy;

A is selected from the group consisting of lower alkyl radicals, lower alkenyl radicals, lower alkynyl radicals, alicyclic hydrocarbon radicals, heterocyclyl radicals and aromatic hydrocarbon radicals, wherein all of said radicals are optionally substituted with hydroxyl, lower alkoxy, lower alkyl, halogen, nitro, carboxyl, trifluoromethyl, amino, acyloxy, and phenyl;

W is selected from the group consisting of hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

Z, Z' are independently selected from the group consisting of hydrogen, lower alkyl radicals, halogen, alkoxy, cyano, sulfonyl, and hydroxy radicals;

m is an integer from 0 to about 6; and n is an integer from 0 to about 3.

R is preferably hydrogen, lower alkyl radicals, lower alkenyl radicals, lower alkynyl radicals, and heterocyclyl radicals were 1 to 2 hetero atoms are nitrogen or oxygen, more preferably R is hydrogen, lower alkyl and heterocyclyl radicals were 1 to 2 heteroatoms are nitrogen, most preferably R is Hydrogen or pyridine.

A is preferably lower alkyl radicals, lower alkenyl radicals, lower alkynyl radicals, or aromatic hydrocarbon radicals, more preferably A is lower alkyl and benzyl.

W is preferably lower alkyl radicals, lower alkenyl radicals, or lower alkynyl radicals, more preferably W is hydrogen and lower alkyl.

Z, Z' are preferably lower alkyl and hydrogen, more preferably Z,Z' are hydrogen.

m is preferably 0 to about 3 more preferably 0.

n is preferably 0.

The invention further relates to pharmaceutical compositions comprising a compound of Formula (I). Such compounds and compositions have usefulness as inhibitors of platelet aggregation.

It is still another object of the invention to provide a method to therapeutically inhibit or modulate platelet aggregation or the like in a mammal in need of such treatment with a compound of the formula I in unit dosage form. Particularly in inhibiting or modulating platelet aggregation by administering an amount between 0.5 mg/kg to 10 mg/kg, preferably 3 mg/kg to an animal in need thereof.

Many other objects and purposes of the invention will be clear from the following detailed description of the invention and examples.

DETAILED DESCRIPTION OF THE INVENTION

A preferred embodiment of the present invention is a compound of the formula I or a pharmaceutically acceptable salt thereof:

wherein R is independently selected from the group consisting of hydrogen, lower alkyl radicals of 1 to about 6 carbon atoms, lower alkenyl radicals of 2 to about 6 carbon atoms, lower alkynyl radicals of 2 to about 8 carbon atoms, alicyclic hydrocarbon radicals of 3 to about 6 carbon atoms, and aromatic hydrocarbon radicals, wherein all of said radicals are optionally substituted with hydroxyl, lower alkoxy, lower alkyl, halogen, nitro, carboxyl, and trifluoromethyl;

or R is a monocyclic or bicyclic heterocyclyl radical in which 1 to about 3 heteroatoms are independently selected from nitrogen or oxygen;

A is selected from the group consisting of lower alkyl radicals, lower alkenyl radicals, lower alkynyl radical, heterocyclyl radicals and aromatic hydrocarbon radicals, wherein all of said radicals are optionally substituted with hydroxyl, lower alkoxy, lower alkyl, halogen, nitro, carboxyl, trifluoromethyl, amino, acyloxy, and phenyl;

W is selected from the group consisting of hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z' are independently selected from the group consisting of hydrogen, lower alkyl radicals, halogen, alkoxy, cyano, sulfonyl, and hydroxy radicals;

m is an integer from 0 to about 3; and n is an integer from 0 to about 3.

Another preferred embodiment of the present invention is a compound of the formula (I) or a pharmaceutically acceptable salt thereof;

wherein R is independently selected from the group consisting of hydrogen, lower alkyl radicals and aromatic hydrocarbon radicals, or R is a monocyclic heterocyclyl radical in which 1 to 2 hetero atoms are nitrogen.

A is selected from the group consisting of lower alkyl radicals, lower alkenyl radicals, lower alkynyl radical, heterocyclyl radicals and aromatic hydrocarbon radicals, wherein all of said radicals are optionally substituted with hydroxyl, lower alkoxy, lower alkyl, halogen, nitro, carboxyl, trifluoromethyl, amino, acyloxy and phenyl;

W is selected from the group consisting of hydrogen and lower alkyl radicals;

Z, Z' are independently selected from the group consisting of hydrogen, lower alkyl radicals, halogen and hydroxy radicals;

m is an integer from 0 to 1; and n is an integer from 0 to 1.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radicals in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyl-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" means a aliphatic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "aromatic hydrocarbon radical" means 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The term "lower alkoxy", alone or in combination, means an alkyl ether radical wherein the term alkyl is an defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "heterocyclyl radical" means a heterocyclyl hydrocarbon radical preferably an aromatic heterocyclyl hydrocarbon radical with 4 to about 10 carbon atoms, preferably about 5 to about 6; wherein 1 to about 3 carbon atoms are replaced by nitrogen, oxygen or sulfur. The "heterocyclyl radical" may be fused to a aromatic hydrocarbon radical or to another heterocyclyl radical. The "heterocyclyl radical" may be saturated, partially saturated, or fully unsaturated. Suitable examples include pyrrolyl, pyridinyl, pyrazolyl, pyrrolyl, triazolyl, pyrimidinyl, pyridazinyl, oxazolyl, thiazolyl, imidazolyl, indoyl, thiophenyl, furanyl, tetrazolyl, 2-pyrrolinyl, 3-pyrrolinyl, pyrrolidinyl, 1,3-dioxolanyl, 2-imidazolinyl, imidazolidinyl, 2-pyrazolinyl, pyrazolidinyl, isoxazolyn, isothiazolyn, 1,2,3-oxadiazolyn, 1,2,3-triazolyn, 1,3,4-thiadiazolyn, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyn, quinolinyl, and the like.

The term "halogen" means fluorine, chlorine, bromine or iodine.

The term "pharmaceutically acceptable salt" refers to a salt prepared by contacting a compound of Formula (I) with an acid whose anion is generally considered suitable for human consumption. Examples of pharmaceutically acceptable salts include the hydrochloride, hydrobromide, hydroiodide, sulfate, phosphate, acetate, propionate, lactate, maleate, oxalate, malate, succinate, tartrate and citrate salts. All of these salts may be prepared by conventional means by reacting, for example, the appropriate acid with the corresponding compound of formula I.

Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine.

Total daily dose administered to a host in single or divided doses may be in amounts, for example, from 0.001 to 100 mg/kg body weight daily and more usually 0.01 to 10 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood that the specific dose level for any particular patient will depend upon a variety of factors including the activity of the specific compound employed, the age, body weight, general health, sex, diets, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectable.

Suppositories for rectal administration of the drug can be prepared by mixing the drug with a suitable nonirritating excipient such as cocoa butter and polyethylene glycols which are solid at ordinary temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more active pharmaceutical agents. When administered as a combination, the therapeutic agents can be formulated as separate compositions which are given at the same time or different times, or the therapeutic agents can be given as a single composition.

In the structures and formulas herein, the bond drawn across a bond of an aromatic ring can be to any available atom on the aromatic ring.

The compound of formula I can exist in various isomeric forms and all such isomeric forms are meant to be included. Tautomeric forms are also included in the invention. Pharmaceutically acceptable salts of such isomers and tautomers are meant to be included as well.

The compounds listed may be prepared by standard synthetic methods combined with methods analogous to solution phase peptide synthesis [see: The Peptides: Analysis, Synthesis, Biology (E. Gross and J. Meienhofer, eds.), (Vol. 1–5, Academic Press, New York)].

General synthetic sequences for preparing the compounds of Formula I are outlined in scheme I and II.

Purification of final compounds can be performed by reverse phase high pressure liquid chromatography or crystallization [*High Performance Liquid Chromatography Protein and Peptide Chemistry*, F. Lottspeich, A. Henscher, K. P. Hupe, eds.) Walter DeGruyter, New York, 1981.

Contemplated equivalents of the general formulas set forth above for the platelet aggregation inhibitors and derivatives as well as the intermediates are compounds otherwise corresponding thereto and having the same general properties wherein one or more of the various R groups are simple variations of the substituents as defined therein, e.g., wherein R is a higher alkyl group than that indicated. In addition, where a substituent is designated as, or can be, a hydrogen, the exact chemical nature of a substituent which is other than hydrogen at that position, e.g., a hydrocarbyl radical or a halogen, hydroxy, amino and the like functional group, is not critical so long as it does not adversely affect the overall activity and/or synthesis procedure.

The chemical reactions described are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. Therefore, the following preferred specific embodiments are to be construed as merely illustrative and not limitative of the remainder of the disclosure in any way whatsoever.

The following examples are provided to illustrate the present invention and are not intended to limit the scope thereof. Those skilled in the art will readily understand that known variations of the conditions and processes of the following preparative procedures can be used to prepare these compounds. All temperatures expressed are in degrees centigrade.

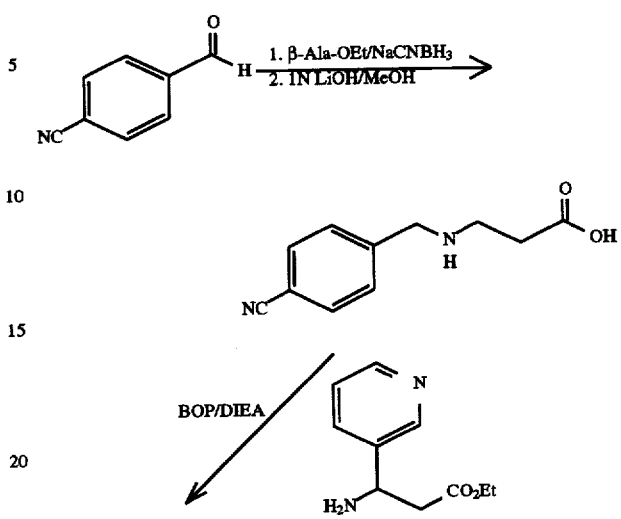

SCHEME II

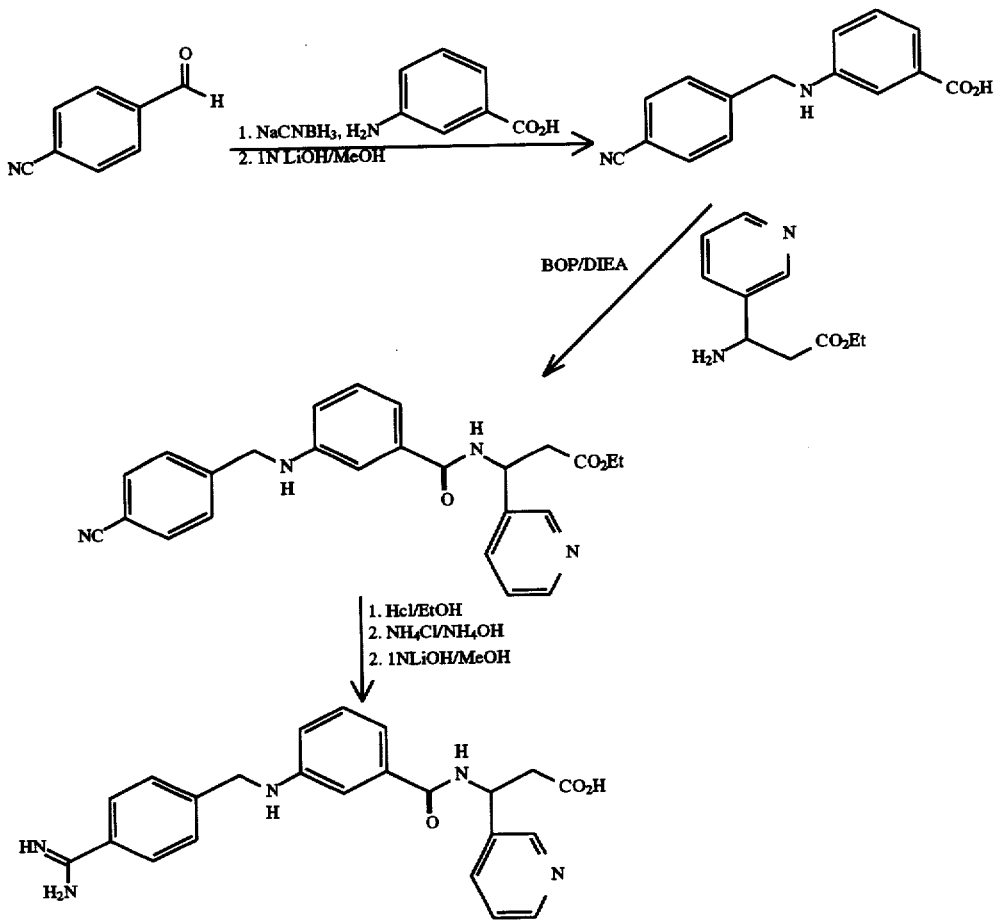

SCHEME I

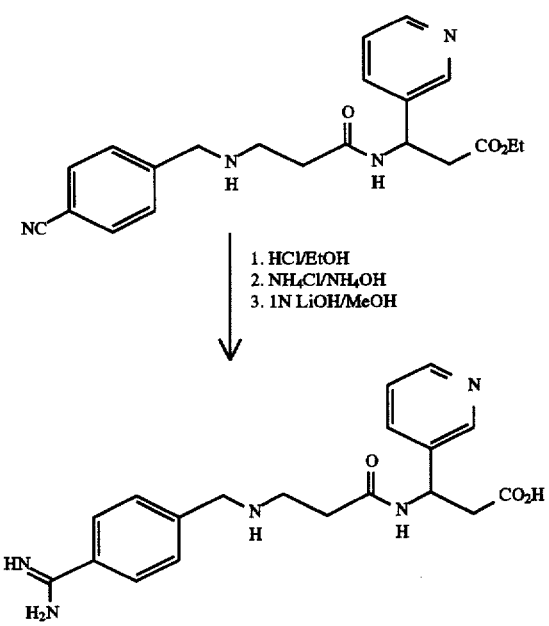

EXAMPLE 1

Ethyl β-[[3-[4-(aminoiminomethyl)benzyl]aminobenzoyl]amino]propanoate

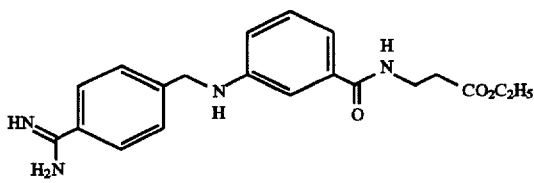

Step 1.
Preparation of 3-[4-cyanobenzyl]aminobenzoic acid 4-cyanobenzaldehyde (0.65 g; 5 mmoles), 3-aminobenzoic acid (0.68 g; 5 mmoles) and sodiumcyanoborohydride (0.35 g; 5 mmols) were stirred in N,N-dimethylformamide (25 ml) containing 1% acetic acid at room temperature for 2 hrs. The product was precipitated out by addition of water. The solid was filtered and dried in vacuo to give 0.95 g white solid. FAB-MS: MH⁺=253.

Step 2.
Preparation of ethyl β-[[3-[4-(aminoiminomethyl)benzyl]aminobenzoyl]amino]propanoate 3-[4-cyanobenzyl]aminobenzoic acid (0.25 g; 1 mmol), β-alanine ethyl ester.HCl (0.15 g; 1 mmol), N,N-diisopropylethylamine (0.26 g; 2 mmoles) and benzotriazol-1-yl-oxy-tris(dimethylamino)phosphonium hexafluorophosphate (0.44 g; 1 mmol) were stirred in N,N-dimethylformamide (25 ml) at room temperature for 1 hr. The reaction mixture was taken down to dryness and the residue was redissolved in ethanol (30 ml). The solution was saturated with HCl gas and allowed to stir overnight. The mixture was taken down to dryness and the residue was redissolved in ethanol (20 ml). To this solution, ammonium chloride (1 g) and ammonium hydroxide (10 ml) were added. The reaction mixture was stirred at room temperature overnight and the solvent was removed under reduced pressure. The residue was purified by HPLC using acetonitrile/water/trifluoroacetic acid system. The desired fractions were collected and lyophilized to give 190 mg of white material. FAB-MS: MH⁺=369.5

Elemental analysis: C₂₀H₂₄N₄O₃.CF₃COOH.2H₂O

|  | C | H | N |
|---|---|---|---|
| Calculated: | 50.96 | 5.50 | 10.82 |
| Found: | 51.35 | 5.18 | 10.66 |

EXAMPLE 2

β-[[3-[4-(aminoiminomethyl)benzyl]aminobenzoyl]amino]propanoic acid

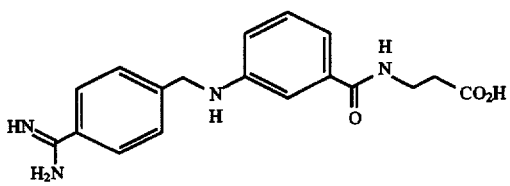

Ethyl β-[[3-[4-(aminoiminomethyl)benzyl]aminobenzoyl]amino]propanoate (75 mg) was treated with 1N lithium hydroxide and methanol (1:1; 20 ml) for 5 min. Methanol was removed under reduced pressure and the residue was purified by HPLC using acetonitrile/water/trifluoroacetic acid system. The desired fractions were collected and lyophilized to give 66 mg of white material. FAB-MS: MH⁺=341.2.

Elemental analysis: C₁₈H₂₀N₄O₃.CF₃COOH.H₂O

|  | C | H | N |
|---|---|---|---|
| Calculated: | 50.87 | 4.87 | 11.86 |
| Found: | 51.19 | 4.39 | 11.70 |

EXAMPLE 3

Ethyl β-[[3-[4-(aminoiminomethyl)benzyl]aminobenzoyl]amino]3-pyridine-propanoate

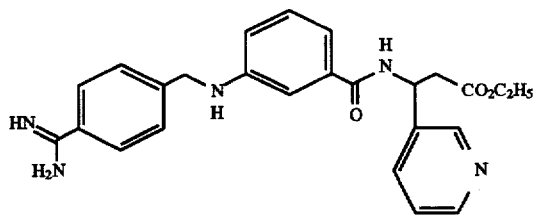

3-[4-cyanobenzyl]aminobenzoic acid (0.5 g; 2 mmoles), ethyl β-amino-β-(3-pyridyl)-propanoate dihydrochloride (0.46 g; 1.7 mmoles), diisopropylethylamine (0.52 g; 4 mmoles) and benzotriazol-1-yl-oxy-tris(dimethylamino)phosphonium hexafluorophosphate (0.88 g; 2 mmoles) were stirred in N,N-dimethylformamide (25 ml) at room temperature for 1 hr. The reaction mixture was taken down to dryness and the residue was redissolved in ethanol (30 ml). The solution was saturated with HCl gas and allowed to stir overnight. The mixture was taken down to dryness and the residue was redissolved in ethanol (20 ml). To this solution, ammonium chloride (1 g) and ammonium hydroxide (10 ml) were added. The reaction mixture was stirred at room temperature for 4 hrs. and the solvent was removed under reduced pressure. The residue was purified by HPLC using acetonitrile/water/trifluoroacetic acid system. The desired fractions were collected and lyophilized to give 530 mg of white material. FAB-MS: MH$^+$=446.3.

Elemental analysis: $C_{24}H_{27}N_5O_3.2CF_3COOH$

|  | C | H | N |
|---|---|---|---|
| Calculated: | 51.76 | 4.34 | 10.40 |
| Found: | 53.01 | 4.69 | 11.45 |

EXAMPLE 4

β-[[3-[4-(aminoiminomethyl)benzyl]aminobenzoyl]amino]-3-pyridinepropanoic acid

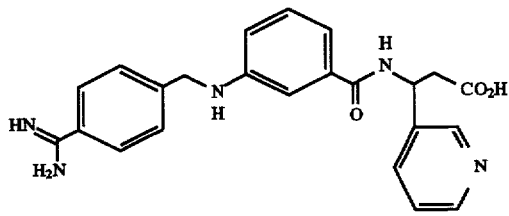

Ethyl β-[[3-[4-(aminoiminomethyl)benzyl]aminobenzoyl]amino]3-pyridine-propanoate (0.35 g; 0.8 mmoles) was treated with 1N lithium hydroxide and methanol (1:1; 20 ml) for 5 min. Methanol was removed under reduced pressure and the residue was purified by HPLC using acetonitrile/water/trifluoroacetic acid system. The desired fractions were collected and lyophilized to give 290 mg of white material. FAB-MS: MH$^+$=418.0.

Elemental analysis: $C_{23}H_{23}N_5O_3.2CF_3COOH.2H_2O$

|  | C | H | N |
|---|---|---|---|
| Calculated: | 47.57 | 4.25 | 10.27 |
| Found: | 46.94 | 3.78 | 9.93 |

EXAMPLE 5

Ethyl β-[[3-[4-(aminoiminomethyl)benzyl]aminopropanoyl]amino]3-pyridinepropanoate

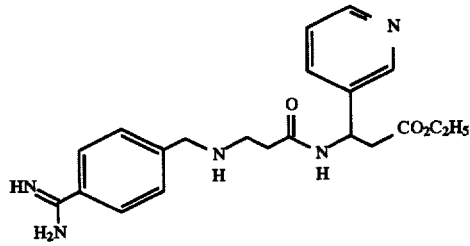

Step 1.
Preparation of 3-[4-cyanobenzyl]aminopropanoic acid
4-cyanobenzaldehyde (0.65 g; 5 mmoles) and β-alanine ethyl ester.HCl (0.76 g; 5 mmoles) were dissolved in N,N-dimethylformamide (10 ml) containing 1% acetic acid. After 10 min., sodiumcyanoborohydride (0.35 g; 5 mmoles) was added to the solution. The reaction mixture was stirred at room temperature for 12 hrs. and taken down to dryness under reduced pressure. The residue was treated with 1N lithium hydroxide/methanol (1:1; 20 ml) for 15 min. Methanol was removed and the pH of the remaining solution was adjusted to pH 5 with 50% acetic acid. The product was purified by HPLC using a linear gradient of acetonitrile/water/trifluoroacetic acid. The desired fractions was collected and lyophilized to give 0.81 g of white solid (79% yield). FAB-MS: MH$^+$=205.1.

Step 2.
Preparation of ethyl β-[[3-[4-(aminoiminomethyl)benzyl]aminopropanoyl]amino]3-pyridinepropanoate 3-[4-cyanobenzyl]aminopropanoic acid (0.41 g; 2 mmoles), ethyl βamino-β-(3-pyridyl)-propanoate dihydrochloride (0.46 g; 1.7 mmoles), N,N-diisopropylethylamine (0.52 g; 4 mmoles) and benzotriazol-1-yl-oxy-tris (dimethylamino)phosphonium hexafluorophosphate (0.88 g; 2 mmoles) were stirred in N,N-dimethylformamide (25 ml) at room temperature for 1 hr. The reaction mixture was taken down to dryness and the residue was purified by HPLC. The lyophilized product was redissolved in ethanol (30 ml). The solution was saturated with HCl gas and allowed to stir overnight. The mixture was taken down to dryness and the residue was redissolved in ethanol (20 ml). To this solution, ammoniumchloride (1 g) and ammonium hydroxide (10 ml) were added. The reaction mixture was stirred at room temperature for 4 hrs and the solvent was removed under reduced pressure. The residue was purified by HPLC using acetonitrile/water/trifluoroacetic acid system. The desired fractions were collected and lyophilized to give 460 mg of white material (57% yield). FAB-MS: MH$^+$=398.2.

Elemental analysis: $C_{21}H_{27}N_5O_3.3CF_3COOH$

|  | C | H | N |
|---|---|---|---|
| Calculated: | 42.80 | 4.22 | 9.24 |
| Found: | 42.95 | 3.59 | 9.42 |

EXAMPLE 6

β-[[3-[4-(aminoiminomethyl)benzyl]aminopropanoyl]amino]-3-pyridinepropanoic acid

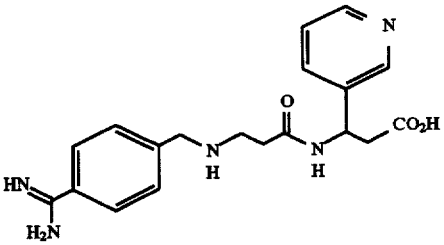

Ethyl β-[[3-[4-(aminoiminomethyl)benzyl]aminopropanoyl]amino]3-pyridine-propanoate (70 mg) was treated with 1N lithium hydroxide and methanol (1:1; 20 ml) for 5 min. Methanol was removed under reduced pressure and the residue was purified by HPLC using acetonitrile/water/trifluoroacetic acid system. The desired fractions were collected and lyophilized to give 50 mg of white material (77% yield). FAB-MS: MH$^+$=370.3.

| Elemental analysis: C₁₉H₂₃N₅O₃.3CF₃COOH | | | |
|---|---|---|---|
| | C | H | N |
| Calculated: | 41.15 | 3.84 | 9.60 |
| Found: | 41.68 | 3.56 | 9.72 |

Further examples prepared by above described methods are the following compounds:

EXAMPLE 7

Ethyl β-[[3-[4-(aminoiminomethyl)benzyl]aminopropanoyl]amino]propanoate; FAB-MS: MH⁺=321

| Elemental analysis: C₁₆H₂₄N₄O₃.2CF₃COOH | | | |
|---|---|---|---|
| | C | H | N |
| Calculated: | 43.79 | 4.74 | 10.21 |
| Found: | 43.39 | 4.37 | 10.34 |

EXAMPLE 8

β-[[3-[4-(aminoiminomethyl)benzyl]aminopropanoyl]amino]propanoic acid; FAB-MS: MH⁺=293

| Elemental analysis: C₁₄H₂₀N₄O₃.2CF₃COOH | | | |
|---|---|---|---|
| | C | H | N |
| Calculated: | 41.53 | 4.23 | 10.76 |
| Found: | 41.16 | 3.74 | 10.88 |

EXAMPLE 9

Ethyl β-[[3-[4-(aminoiminomethyl)benzyl]piperidylcarbonyl]amino]-3-pyridine-propanoate; FAB-MS: MH⁺=438

EXAMPLE 10

β(S)-[[N-3-[4-(aminoiminomethyl)benzyl]piperidylcarbonyl]amino]-3-pyridine-propanoic acid; FAB-MS: MH⁺=410

EXAMPLE 11

β(R)-[[N-3-[4-(aminoiminomethyl)benzyl]piperidylcarbonyl]amino]-3-pyridine-propanoic acid. FAB-MS: MH⁺=410

| Elemental analysis: C₂₂H₂₇N₅O₃.3CF₃COOH.H₂O | | | |
|---|---|---|---|
| | C | H | N |
| Calculated: | 43.69 | 4.16 | 9.10 |
| Found: | 43.02 | 4.86 | 9.10 |

In-Vitro Platelet Aggregation in PRP

Healthy male or female dogs were fasted for 8 hours prior to drawing blood; then 30 ml whole blood was collected using a butterfly needle and 30 cc plastic syringe with 3 ml or 0.129M buffered sodium citrate (3.8%). The syringe was rotated carefully as blood was drawn to mix the citrate. Platelet-rich plasma (PRP) was prepared by centrifugation at 975 x g for 3.17 minutes at room temperature allowing the centrifuge to coast to a stop without braking. The PRP was removed from the blood with a plastic pipette and placed in a plastic capped, 50 mL Corning conical sterile centrifuge tube which was held at room temperature. Platelet poor plasma (PPP) was prepared by centrifuging the remaining blood at 2000 x g for 15 minutes at room temperature allowing the centrifuge to coast to a stop without braking. The PRP was adjusted with PPP to a count of 2–3×10⁸ platelets per mL. 400 uL of the PRP preparation and 50 uL of the compounds solution to be tested or saline were preincubated for 1 minute at 37° C. in a BioData, Horsham, Pa.). 50 uL of adenosine 5' diphosphate (ADP) (50 um final concentration) was added to the cuvettes and the aggregation was monitored for 1 minute. All compounds are tested in duplicate. Results are calculated as follows: Percent of control=[(maximal OD minus initial OD of compound) divided by (maximal OD minus initial OD of control saline) ]×100. The % inhibition=100–(percent of control).

The compounds tested and their median inhibitory concentrations ($IC_{50}$) are recorded in Table I. $IC_{50}$'s (dosage at which 50% of platelet aggregation is inhibited) were calculated by linear regression of the dose response curve. The assay results for the compounds of Examples 1 to 6 are set forth in Table I below.

TABLE I

| Example | Dog PRP $IC_{50}$ or % Inh. |
|---|---|
| 1 | NT |
| 2 | 28% at $10^{-5}$M |
| 3 | NT |
| 4 | $6.8 \times 10^{-6}$M |
| 5 | NT |
| 6 | $8.0 \times 10^{-7}$M |

NT - not tested

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound or a pharmaceutically acceptable salt thereof having the formula

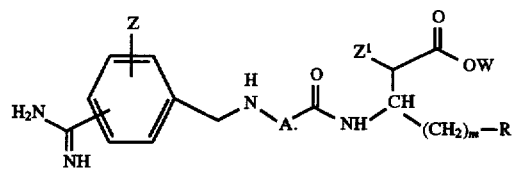

wherein R is independently selected from the group consisting of hydrogen, lower alkyl radicals of 1 to about 6 carbon atoms and monocyclic aromatic radicals;

A is a monocyclic aromatic hydrocarbon radical;

W is selected from the group consisting of hydrogen and lower alkyl radicals;

Z and Z' are independently selected from the group consisting of hydrogen, lower alkyl radicals, halogen, alkoxy, cyano, sulfonyl, carboxyl and hydroxyl radicals; and m is an integer from 0 to about 3.

2. A compound according to claim 1 selected from the group consisting of
(a) ethyl β-[[-3-[4-aminoiminomethyl)benzyl]aminobenzoyl]amino]propanoate;
(b) β-[[3-[4-(aminoiminomethyl)benzyl]aminobenzoyl]amino]propanoic acid;
(c) ethyl β-[[3-[4-aminoiminomethyl)benzyl]aminobenzoyl]amino]-3-pyriidinepropanoate; and
(d) β-[[3-[4-(aminoiminomethyl)benzyl]aminobenzoyl]amino]-3-pyridinepropanoic acid.

3. A compound or a pharmaceutically acceptable salt thereof having the formula

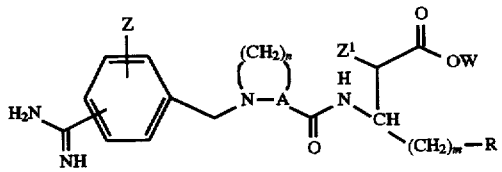

wherein R is independently selected from the group consisting of hydrogen, lower alkyl radicals of 1 to about 6 carbon atoms and monocyclic aromatic radicals;

A is a lower alkyl radical;

W is selected from the group consisting of hydrogen and lower alkyl radicals;

Z and Z' are independently selected from the group consisting of hydrogen, lower alkyl radicals, halogen, alkoxy, cyano, sulfonyl, carboxyl and hydroxyl radicals;

m is an integer from 0 to about 3; and n is 1.

4. A compound according to claim 3 selected from the group consisting of
(a) ethyl β-[[N-3-[4-(aminoiminomethyl)benzyl]piperidyl carbonyl]amino]-3-pyridinepropanoate;
(b) β(S)-[[N-3-[4-(aminoiminomethyl)benzyl]piperidyl carbonyl]amino]]-3-pyridinepropanoic acid; and
(c) β(R)-[[N-3-[4-(aminoiminomethyl)benzyl]piperidyl carbonyl]amino]]-3-pyridinepropanoic acid.

5. A pharmaceutical composition comprising at least one non-toxic pharmaceutically acceptable carrier and at least one compound according to claims 1, 2, 3, or 4 together with said carrier.

6. A method of treating a mammal to inhibit platelet aggregation comprising administering a therapeutically effective amount of at least one compound of claims 1, 2, 3 or 4 to a mammal in need of such treatment.

* * * * *